United States Patent
Goodwin et al.

[11] Patent Number: 6,063,363
[45] Date of Patent: May 16, 2000

[54] TREATMENT FOR UPPER RESPIRATORY TRACT INFECTIONS WITH POTASSIUM SALTS

[76] Inventors: Gary J Goodwin; Roberta L Goodwin, both of 31 Brushwood Dr., Shirley, N.Y. 11967-4009

[21] Appl. No.: 08/863,141

[22] Filed: May 27, 1997

[51] Int. Cl.[7] ................................ A61K 9/12; A61K 9/20
[52] U.S. Cl. ......................... 424/45; 424/610; 424/439; 424/464; 514/937; 514/944; 514/969
[58] Field of Search .............................. 424/610, 45, 439, 424/464; 514/944, 937, 969

[56] References Cited

U.S. PATENT DOCUMENTS 4,731,362  3/1988  Hamashima et al. ..................... 514/20
4,879,296  11/1989  Daluge et al. ............................. 424/45

*Primary Examiner*—Raj Bawa
*Attorney, Agent, or Firm*—Michael I. Kroll

[57] ABSTRACT

A method for alleviating the symptoms of an upper respiratory tract infection in humans employs the application of a composition containing, in a pharmaceutically acceptable carrier, 0.1 to 3.0 weight percent of a potassium salt such as one or more of potassium acetate, potassium aluminate, potassium arsenite solution, potassium bicarbonate, potassium bisulfate, potassium bitartarate, potassium bromide, potassium carbonate, potassium chloride, potassium citrate, potassium gluconate, potassium glycerophosphate, potassium iodate, potassium iodide, potassium manganate, potassium permanganate, potassium phosphate monobasic, potassium phosphate dibasic, potassium phosphate tribasic and potassium phosphite.

5 Claims, No Drawings

TREATMENT FOR UPPER RESPIRATORY TRACT INFECTIONS WITH POTASSIUM SALTS

BACKGROUND OF THE INVENTION

1. Field of the Invention

The instant invention relates generally to compositions and methods for treating and preventing upper respiratory tract disorders and the symptoms associated therewith. More specifically, the invention relates to compositions and methods for treating and preventing upper respiratory tract infections and other disorders via the administration of potassium containing compositions. These compositions and methods of use are effective in treating and preventing the symptoms of upper respiratory tract infections, for example, the common cold, rhinitis, sinusitis, in addition to disorders such as asthma and other such conditions.

2. Description of the Prior Art

Human upper respiratory tract infections (URTIs) and disorders have caused widespread suffering for centuries. These infections are generally caused by microorganisms such a bacteria and viruses which can be either airborne or transmitted via direct contact. The early stages of infection are usually characterized by congestion of the sinuses, often accompanied by profuse mucous production. Subsequently, the infection can spread downward to the throat, bronchi and lungs. In some cases, the infection is limited to the sinuses and may persist for some time.

While many treatments have been proposed and utilized for treating and/or preventing upper respiratory tract infections and their symptoms, their efficacy and side effects have left much to be desired. Excess mucous production is often treated with antihistamines, and congestion is generally treated with topical vasoconstricting agents. Long term sinus problems are currently treated with corticosteroid-containing preparations in an effort to keep the sinuses clear and thus reduce the development of infection either viral or bacterial. Side effects of these treatments is always of concern, however. For example, antihistamine use is often associated with drowsiness. Topical vasoconstrictors can be irritating and often can exhibit a physiologically addicting effect whereby the sinuses congest when the vasoconstrictor is withdrawn. There is also significant concern over the long term effects of systemic corticosteroids use.

BRIEF SUMMARY OF THE INVENTION

The present invention is concerned with a composition and method for treating and preventing upper respiratory tract infections and other disorders and the symptoms associated therewith.

A primary object of the present invention is to provide an effective treatment for significantly reducing the symptoms of upper respiratory tract infections and other disorders.

It is a further object of the present invention is to provide an effective treatment for preventing the symptoms of upper respiratory tract infections and other disorders.

Another object of the present invention is to provide a potassium containing composition effective in treating and preventing upper respiratory tract infections and disorders and the symptoms associated therewith.

An additional object of the present invention is to provide a potassium containing composition for treating and preventing upper respiratory tract infections and disorders and the symptoms associated therewith which is non-toxic and has considerably less liability for adverse side effects than existing treatments.

It is a further object of the present invention to provide a potassium containing composition for treating and preventing upper respiratory tract infections and disorders and the symptoms associated therewith which is simple and inexpensive to formulate.

Another object of the present invention is to provide a potassium containing composition for treating and preventing upper respiratory tract infections and disorders and the symptoms associated therewith which may be used by the patient in an easy and convenient manner.

The foregoing and other objects, advantages and characterizing features will become apparent from the following description of certain illustrative embodiments of the invention.

The novel features which are considered characteristic for the invention are set forth in the appended claims. The invention itself, however, both as to its formulation and its method of use, together with additional objects and advantages thereof, will be best understood from the following description of the specific embodiments.

DETAILED DESCRIPTION OF THE PREFERRED EMBODIMENTS

Potassium (atomic symbol K) is an alkaline metallic element, occurring abundantly in nature. Because of its high reactivity, however, it is always found in chemical composition form, such as part of a salt. Its salts are commonly used in medicine for therapeutic uses, and in intracellular fluid it is essential for proper maintenance of acid-base isotonicity and the electrodynamic characteristics of the cell. Potassium is an important activator in many enzymatic reactions and is essential to a number of physiologic processes including transmission of nerve impulses, contracting of cardiac, smooth and skeletal muscles, gastric secretion, renal function, tissue synthesis and carbohydrate metabolism. Once it is absorbed, potassium first enters the extracellular fluid and is then actively transported into the cells where its concentration is up to 40 times that outside of cells. In healthy adults, plasma potassium concentrations generally range from 3.5 to 5 mEq/L. Potassium is excreted mainly by the kidneys; except for severe renal impairment, hyperkalemia or potassium toxicity is not likely to result from topical administration of potassium.

On the basis of the clinical observation described above, a trial was conducted by the inventors, whereby salts of potassium were administered by different routes to achieve potassium saturation of the cells and tissues which are involved in pathology of upper respiratory tract infections.

The present invention provides a potassium containing composition for introduction into the lungs and/or nasal areas and/or the oral cavity as a gargle for areas of the patient which evidence the symptoms of an upper respiratory tract infection or other disorder. The potassium containing composition will generally be in the form of a potassium salt. Such potassium salts include, but are not limited to, one or more of the following.

potassium acetate ($KC_2H_3O_2$)
potassium aluminate ($K_2Al_2O_4$)
potassium arsenite solution
potassium bicarbonate ($KHCO_3$)
potassium bisulfate ($KHSO_4$)
potassium bitartarate ($KC_4H_5O_6$)
potassium bromide (KBr)
potassium carbonate ($K_2CO_3$)

potassium chloride (KCl)
potassium citrate ($K_3C_6O_7H_5$)
potassium gluconate ($KC_6O_7H_{11}$)
potassium glycerophosphate ($KC_3P_2O_6H_7$)
potassium iodate ($KIO_3$)
potassium iodide (KI)
potassium manganate ($KMnO_4$)
potassium permanganate ($K_2MnO_4$)
potassium phosphate monobasic ($KH_2PO_4$)
potassium phosphate dibasic ($K_2HPO_4$)
potassium phosphate tribasic ($K_3PO_4$)
potassium phosphite ($K_2HPO_3$)

Any of the above listed salts of potassium by itself, or in combination with others, are used to prepare the composition of the present invention as a liquid solution, nasal spray, inhalant, emulsion, cream, ointment, suspension, mixture, lozenge or gel preparation. The preferred potassium containing compounds are selected from one or more of potassium phosphate monobasic, potassium phosphate dibasic and potassium chloride. The composition will preferably contain from about 0.1 to about 3.0 percent of the potassium containing compound(s), by weight. The repeated application of these compositions to the afflicted areas of the patient (e.g. the nasal passages, throat, lungs) has provided potassium saturation of the cells and tissues locally, where the cells and tissues are involved in pathology of upper respiratory tract infections. Conventional solvents, emulsifiers, bases and vehicles are used to facilitate intramucosal absorption.

The present invention is useful in treating upper respiratory infections or disorders, particularly those associated with an inflammatory response of mucous membrane-containing tissues. These compositions are very effective in penetrating the excessive or clogged mucous, such as, for example, upper sinus congestions and related conditions. This has shown to be of great benefit to persons suffering from conditions such as chronic sinus infections. The compositions of the invention penetrate very high in the sinus cavities and relieve areas of trapped or encapsulated mucous congestion. Once the sinuses have been thus drained, moreover, it has been found that other secondary symptoms (headaches, dizziness, tinnitus, recurring infections etc.) are greatly alleviated or even eliminated.

Owing to their efficacy in penetrating congestion and reducing inflammation, the present compositions find particular utility in treating conditions such as asthma which are intimately associated with congestion and inflammation. The compositions can be readily administered to the lungs via oral inhalation by conventional means such as aerosol inhalers, nebulizers and the like.

The compositions of the invention have also shown utility in treating cold sores (normally associated with herpes simplex virus), and accordingly should also find utility in treating other of the various herpes infections.

With regard to the mechanism of action of the present invention, it is surmised that the inventive compositions, by virtue of their low (hypotonic) concentration of only potassium-based salts, would create a concentration gradient across the cell membranes, and thus would tend to draw sodium ions out of the cells and allow replacement with potassium ions, resulting in an atypical intracellular ionic distribution. This decrease in intracellular sodium and increase in intracellular potassium, and the corresponding atypical intracellular ionic distribution, would likely act to inhibit normal cellular activity in very active cells, such as reproducing pathogenic organisms, thus inhibiting reproduction of the pathogens. The hypotonicity of the inventive compositions may be essential in order to motivate the transfer of sodium out of the cells and to allow the more active potassium ion to enter in higher concentrations than would otherwise be possible without damage to normal cells.

It is further theorized that the ionic imbalance caused by the application of the inventive compositions would tend to draw the body's own defense mechanisms to the infected area and accordingly further reduce or eliminate the growth of the pathogenic organisms. The antiinflammatory action of the potassium salts would also seem to add to the beneficial effect.

The hypotonicity of the compositions of the invention enhances their ability to stimulate the transfer of sodium out of infected cells and to allow the more mobile potassium ion to enter the cells in concentrations higher than would otherwise be possible without damage to the cells.

EXAMPLE 1

A composition of the present invention was prepared by combining the following potassium containing compounds in a base solution of purified water:

| | |
|---|---|
| potassium phosphate monobasic | 0.05 percent; |
| potassium phosphate dibasic | 0.07 percent; and |
| potassium chloride | 0.08 percent. |

A potassium containing formulation was placed into a nasal spray device and used like any ordinary nasal spray by a patient suffering from an upper respiratory infection localized and deep-seated in the sinuses. Initial effects were of significant lessening of both nasal congestion and production of excess mucous. Continued use continued to alleviate the symptoms and there was no apparent tolerance factor which has been observed in other compositions (i.e. corticosteroids and vasoconstrictors). After several months of use there did not appear to be any adverse effects. Most importantly, the patient has not been afflicted with any sinus infection, or common cold or related illness, since regular use of the inventive composition. The composition is not used continuously, but is administered either 1) when URTI symptoms first appear, or 2) when the patient has been exposed to, and is therefore at higher risk of developing, such an infection. It is preferred that the inventive composition be administered as soon as possible after exposure. If symptoms start, a more frequent use of the invention is preferred until all symptoms subside, after which only occasional use is needed.

Volunteers were provided with samples and instructed to use the invention at first sign of any cold symptoms. If they were already suffering, they were instructed to administer the composition as needed to relieve their symptoms. All have reported success regarding treatment of preexisting condition and also have not suffered additional symptoms when the invention was used according to the directions to use at the first sign of symptoms and/or immediately after apparent exposure. The volunteers have not exhibited any adverse reaction during or after the trial, by periodic assessments.

It will be understood that each of the elements described above, or two or more together, may also find a useful application in other types of applications differing from the type described above. While the invention has been illustrated and described as embodied in a composition and method for treating/preventing upper respiratory infections, it is not intended to be limited to the details shown, since it will be understood that various omissions, modifications, substitutions and changes in the forms and details of the formulation illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by Letters Patent is set forth in the appended claims.

What is claimed is:

1. A method for treating an upper respiratory tract infection comprising the step of applying to affected nasal passages, throat or lungs a composition in the form selected from the group consisting of liquid solution, aerosols, emulsions, ointment, lozenge and gel preparation, said composition consisting essentially of a potassium salt in a pharmaceutically acceptable carrier, said potassium salt being present from about 0.1 to about 3.0 percent of the composition by weight, and wherein said potassium salt is selected from the group consisting of potassium acetate, potassium aluminate, potassium arsenite solution, potassium bicarbonate, potassium bisulfate, potassium bitartarate, potassium bromide, potassium carbonate, potassium chloride, potassium citrate, potassium glucontate, potassium glycerophosphate, potassium iodate, potassium iodide, potassium manganate, potassium permanganate, potassium phosphate monobasic, potassium phosphate dibasic, potassium phosphate tribasic and potassium phosphite.

2. A method as defined in claim 1, wherein said potassium salt is selected from the group consisting of potassium phosphate monobasic, potassium phosphate dibasic and potassium chloride.

3. A method as defined in claim 2, wherein said composition comprises potassium phosphate monobasic, potassium phosphate dibasic and potassium chloride in a pharmaceutically acceptable carrier.

4. A method as defined in claim 3, wherein said composition comprises about 0.05 weight percent potassium phosphate monobasic, about 0.07 weight percent potassium phosphate dibasic, and about 0.08 weight percent potassium chloride.

5. A method as defined in claim 4, wherein said pharmaceutically acceptable carrier is water.

* * * * *